(12) United States Patent
Armitage et al.

(10) Patent No.: US 6,514,953 B1
(45) Date of Patent: Feb. 4, 2003

(54) CALCIUM (3S) TETRAHYDRO-3-FURANYL (1S,2R)-3-[[(4-AMINOPHENYL)SULFONYL] (ISOBUTYL)AMINO]-1-BENZYL-2-(PHOSPHONOOXY)PROPYLCARBAMATE

(75) Inventors: Ian Gordon Armitage, Arlesey (GB); Andrew David Searle, Stevenage (GB); Hardev Singh, Dartford (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/744,051
(22) PCT Filed: Jul. 15, 1999
(86) PCT No.: PCT/EP99/04991
§ 371 (c)(1), (2), (4) Date: Apr. 20, 2001
(87) PCT Pub. No.: WO00/04033
PCT Pub. Date: Jan. 27, 2000

(30) Foreign Application Priority Data

Jul. 18, 1998 (GB) .............................. 9815567

(51) Int. Cl.$^7$ .......................... A61K 31/665; C07F 9/06
(52) U.S. Cl. ............................................ 514/99; 549/218
(58) Field of Search ................. 548/100; 549/218; 514/99

(56) References Cited

FOREIGN PATENT DOCUMENTS

JP 58-219189 * 12/1983

* cited by examiner

Primary Examiner—Alan L. Rotman
Assistant Examiner—Binta Robinson
(74) Attorney, Agent, or Firm—Karen L. Prus

(57) ABSTRACT

The invention relates to calcium (3S) tetrahydro-3-furanyl (1S,2R)-3-[[(4-aminophenyl)sulfonyl](isobutyl)amino]-1-benzyl-2-(phosphonooxy)propylcarbamate, to processes for its preparation, and to its use in the treatment of diseases caused by retroviruses.

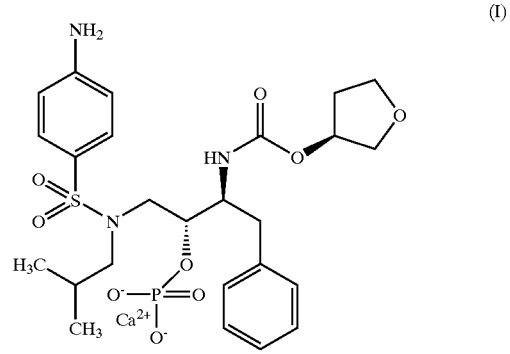

20 Claims, 1 Drawing Sheet

Figure 1:
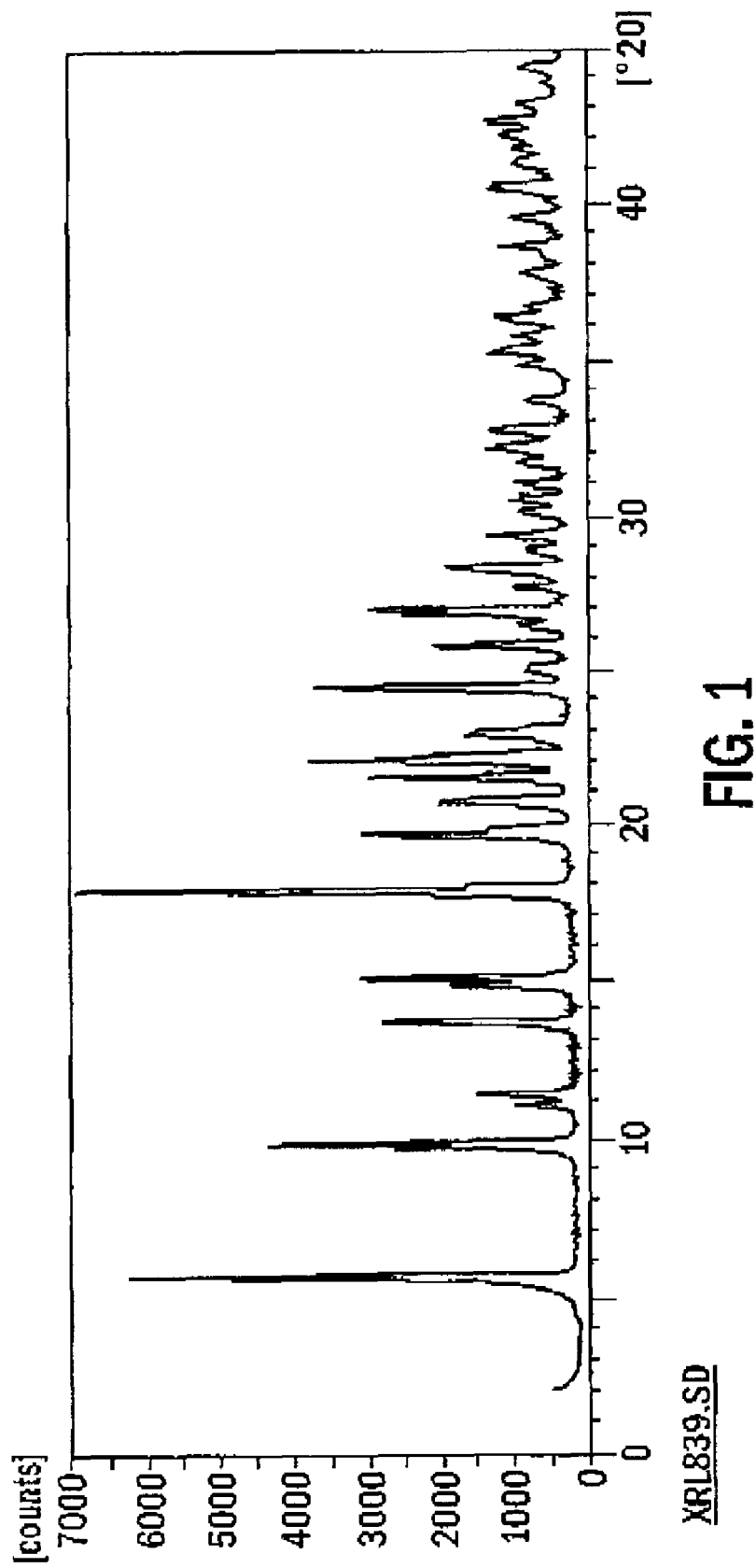

CALCIUM (3S) TETRAHYDRO-3-FURANYL (1S,2R)-3-[[(4-AMINOPHENYL)SULFONYL] (ISOBUTYL)AMINO]-1-BENZYL-2-(PHOSPHONOOXY)PROPYLCARBAMATE

This application is filed pursuant to 35 U.S.C. §371 as a United States National Phase Application of International Application No. PCT/EP99/04991 filed Jul. 15, 1999, which claims priority from GB9815567.4 filed Jul. 18, 1998.

BACKGROUND OF THE INVENTION

The present invention relates to the antiviral compound calcium (3S) tetrahydro-3-furanyl (1S,2R)-3-[[(4-aminophenyl)sulfonyl](isobutyl)amino]-1-benzyl-2-(phosphonooxy)propylcarbamate, pharmaceutical compositions comprising it, its use in the treatment of retroviral infections, and processes for its preparation.

Virus-encoded proteases, which are essential for viral replication, are required for the processing of viral protein precursors. Interference with the processing of protein precursors inhibits the formation of infectious virions. Accordingly, inhibitors of viral proteases may be used to prevent or treat chronic and acute viral infections.

A new antiviral compound, (3S) tetrahydro-3-furanyl (1S,2R)-3-[[(4-aminophenyl)sulfonyl](isobutyl)amino]-1-benzyl-2-(phosphonooxy)propylcarbamate, described in PCT/US98/04595, has HIV aspartyl protease inhibitory activity and is particularly well suited for inhibiting HIV-1 and HIV-2 viruses. Moreover, (3S) tetrahydro-3-furanyl (1S,2R)-3-[[(4-aminophenyl)sulfonyl](isobutyl)amino]-1-benzyl-2-(phosphonooxy)propylcarbamate has increased solubility in the pH range of the gastro-intestinal tract compared to the HIV protease inhibitor [3S-[3R*(1R*,2S*)]]-[3-[[(4-aminophenyl)sulfonyl](2-methyl-propyl)amino]-2-hydroxy-1-phenylmethyl)propyl]-tetrahydro-3-furanyl ester (amprenavir, 141W94). Amprenavir, which has poor solubility and is thus available as a solution in gel capsules and has a high pill burden. This new HIV protease inhibitor with its increased solubility thus has the potential to reduce the perceived pill burden and may be formulated as a tablet.

However, attempts to find a stable crystalline form of (3S) tetrahydro-3-furanyl (1S,2R)-3-[[(4-aminophenyl)sulfonyl] (isobutyl)amino]-1-benzyl-2-(phosphonooxy) propylcarbamate suitable for formulation proved problematic. A range of salts of the phosphoric acid were made (for example, di-sodium, di-potassium, magnesium, zinc, ethylene diamine, piperazine). Of these, the piperazine salt was a crystalline solid, but had the practical disadvantage of likely toxicity at the anticipated dose. Surprisingly, we have found that the calcium salt, calcium (3S) tetrahydro-3-furanyl (1S,2R)-3-[[(4-aminophenyl)sulfonyl](isobutyl)amino]-1-benzyl-2-phosphonooxy)propylcarbamate, has a stable crystalline form. Detailed further examination revealed that this salt has advantageous properties making it suitable for formulation into tablets. Thus the compound of the present invention provides an opportunity to reduce the pill burden associated with some HIV protease inhibitors.

The structure of calcium (3S) tetrahydro-3-furanyl (1S,2R)-3-[[(4-aminophenyl)sulfonyl](isobutyl)amino]-1-benzyl-2-(phosphonooxy)propylcarbamate, a compound of formula (I), is shown below:

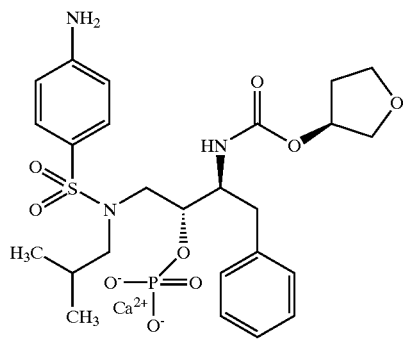

(I)

We have now found that the compound of formula (I) can be prepared in crystalline form, exhibiting particularly good pharmaceutical properties.

DETAILED DESCRIPTION OF THE INVENTION

According to a first aspect of the invention there is provided the compound of formula (I) in crystalline form, hereinafter referred to as Form (I).

The invention relates to Form (I) of the compound of formula (I) in crystalline form. Typically, Form (I) contains about 4 to 5 moles of water. However, in any batch containing Form (I) of the compound of formula (I) there may also be other solvated crystalline forms of the compound of formula (I).

Solid State Form (I) of the compound of formula (I) can be characterised by it's X-ray powder diffraction pattern, shown in FIG. 1. Diffraction traces were obtained using a Phillips PW1800 diffractometer (serial DY701) and Cu K α radiation. X-ray intensities were measured at 0.02° increments for 4 second intervals using a scintillation counter, between values of 2 and 45° 2θ. Intense diffraction peaks characteristic of Form (I) may occur at the following approximate 2theta angles (using copper K α X-radiation): 5.735, 9.945, 11.500, 13.780, 14.930, 15.225, 17.980, 19.745, 21.575, 22.170, 24.505, and 27.020. Further details are presented in Table 1.

It will be appreciated by those skilled in the art that the compound of formula (I) may be in the form of a solvate, for example a hydrate.

According to a further aspect, the present invention provides a process for the production of the compound of formula (I) in a crystalline form, said process comprising the reaction of a compound of formula (II)

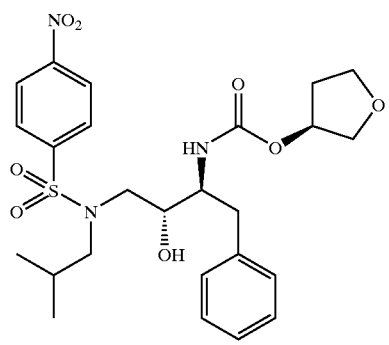

(II)

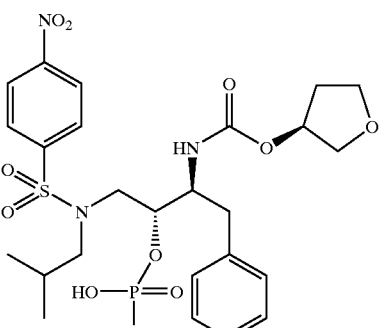

(IV)

with a phosphorylating agent, for example phosphorus oxychloride, phosphorus pentachloride, or dibenzylchlorophosphate, in the presence of a base, for example pyridine, triethylamine or diisopropylethylamine, and optionally in the presence of a solvent, for example methylisobutylketone or dichloromethane; followed by reduction, typically of the sodium salt formed in aqueous solution by addition of sodium bicarbonate, sodium carbonate or sodium hydroxide, with a reducing agent, for example formic acid or hydrogen with palladium/ or platinum/carbon catalyst, in the presence of a suitable solvent, for example water, ethyl acetate, isopropanol, acetone, methanol, industrial methylated spirit or a mixture of two or more of the above solvents; followed by the addition of water and a source of calcium ions, for example calcium acetate, calcium chloride or calcium hydroxide, optionally in the presence of an additional solvent selected from the above-mentioned list.

In a further aspect, the present invention also provides a process for the production of the compound of formula (I), comprising dissolving a compound of formula (III)

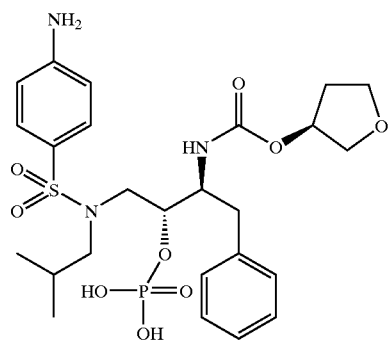

(III)

in a suitable solvent, for example isopropanol, methanol or industrial methylated spirit, and adding to the solution water and a source of calcium ions, for example calcium acetate, calcium chloride or calcium hydroxide.

In a further aspect, the present invention also provides a process for the production of the compound of formula (I), comprising the reduction of a compound of formula (IV), typically of the sodium salt formed in aqueous solution by addition of sodium bicarbonate, sodium carbonate or sodium hydroxide in the presence of a suitable reducing agent, for example formic acid or hydrogen with palladium/ or platinum/carbon catalyst, in the presence of a suitable solvent, for example water, ethyl acetate, isopropanol, acetone, methanol industrial methylated spirit or a mixture of two or more of the above solvents; followed by the addition of water and a source of calcium ions, for example calcium acetate, calcium chloride or calcium hydroxide, optionally in the presence of an additional solvent selected from the above-mentioned list.

It will be appreciated by those skilled in the art that each step may be followed by a standard isolation and purification procedure such as those detailed in the examples hereinafter.

The compound of formula (I) thus obtained may optionally be further purified by recrystallisation from an appropriate solvent, for example industrial methylated spirit, acetone, methanol or isopropanol and mixtures thereof with water, preferably a mixture of industrial methylated spirit and water.

A further optional purification step may be carried out by heating a slurry of the product in water to a temperature in the range 70–99° C., preferably 85–97° C., most preferably 90–95° C., for about 2.5–6 hours, preferably 3–5 hours, most preferably 4 hours, followed by cooling to ambient temperature and harvesting the solid.

The compound of formula (II) may be prepared by any method known in the art, but preferably by the methods described in WO94/05639, incorporated herein by reference hereto.

The compound of formula (III) may be prepared by reaction of a compound of formula (II) with a phosphorylating agent, for example phosphorus oxychloride, phosphorus pentacloride or dibenzylchlorophosphate, in the presence of a base, for example pyridine, triethylamine or diisopropylethylamine, and optionally in the presence of a solvent, for example methylisobutylketone or dichloromethane; followed by reduction, typically of the sodium salt formed in aqueous solution by addition of sodium bicarbonate, sodium carbonate or sodium hydroxide, with a reducing agent, for example formic acid or hydrogen with a palladium/ or platinum/carbon catalyst; in the presence of a suitable solvent, for example water, ethyl acetate, isopropanol, methanol, acetone, industrial methylated spirit or a mixture of two or more of the above solvents.

The compound of formula (IV) may be prepared by the reaction of a compound of formula (II) with a phosphorylating agent, for example phosphorus oxychloride or phosphorus pentachloride, in the presence of a base, for example pyridine, triethylamine or diisopropylethylamine and optionally in the presence of a solvent, for example methylisobutylketone or dichloromethane.

Preferably the phosphorylating agent is phosphorus oxychloride. Preferably the base is pyridine. Preferably the solvent is methyl isobutylketone.

Preferably the reducing agent is hydrogen with a palladium on carbon catalyst with a 5–10% loading of palladium. Preferably the solvent is a mixture of industrial methylated spirit and water The present invention also provides the compound of formula (I) for use in medical therapy, for example in the treatment of a viral disease in an animal, for example, a human. The compound is especially useful for the treatment of diseases caused by retroviruses, such as HIV infections, for example, Acquired Immune Deficiency Syndrome (AIDS) and AIDS-related complex (ARC) as well as diseases caused by hepatitis B and hepatitis C.

In addition to its use in human medical therapy, the compound of formula (I) can be administered to other animals for treatment of viral diseases, for example to other mammals.

The present invention also provides a method for the treatment of a viral infection, particularly a retrovirus infection such as an HIV infection, in an animal, for example, a mammal such as a human, which comprises administering to the animal an effective antiviral amount of the compound of formula (I).

The present invention also provides the use of the compound of formula (I) in the preparation of a medicament for the treatment of a viral infection, particularly a retrovirus infection such as an HIV infection.

The compound of formula (I), also referred to herein as the active ingredient, may be administered by any route appropriate to the condition to be treated, but the preferred route of administration is oral. It will be appreciated however, that the preferred route may vary with, for example, the condition of the recipient.

For each of the above-indicated utilities and indications the amounts required of the active ingredient (as above defined) will depend upon a number of factors including the severity of the condition to be treated and the identity of the recipient and will ultimately be at the discretion of the attendant physician or veterinarian. In general however, for each of these utilities and indications, a suitable effective dose will be in the range of 0.1 to 150 mg per kilogram body weight of recipient per day, advantageously in the range of 0.5 to 70 mg per kilogram body weight per day, preferably in the range of 0.5 to 50 mg per kilogram body weight per day (unless otherwise indicated, all weights of the active ingredient are calculated with respect to the free base of the compound of formula (I)). The desired dose is preferably presented as one, two, three or four or more subdoses administered at appropriate intervals throughout the day. These sub-doses may be administered in unit dosage forms, for example, containing about 25 to 2000 mg, preferably about 50, 100, 150, 200, 250, 300, 450, 500, 570, 750 or 1000 mg of active ingredient per unit dose form.

While it is possible for the active ingredient to be administered alone, it is preferable to present it as a pharmaceutical formulation. The formulation comprises the active ingredient as above defined, together with one or more pharmaceutically acceptable excipients thereof and optionally other therapeutic ingredients. The excipient(s) must be "acceptable" in the sense of being compatible with the other ingredients of the formulation and not deleterious to the recipient thereof.

The formulations include those suitable for oral administration and may conveniently be presented in unit dosage form prepared by any of the methods well known in the art of pharmacy. Such methods include the step of bringing into association the active ingredient with the carrier which constitutes one or more accessory ingredients. In general, the formulations are prepared by uniformly and intimately bringing in to association the active ingredient with liquid carriers or finely divided solid carriers or both, and then, if necessary, shaping the product.

Formulations of the present invention suitable for oral administration may be presented as discrete units such as capsules, cachets, sachets of granules or tablets (such as a swallowable, dispersible or chewable tablet) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored any may be formulated so as to provide slow or controlled release of the active ingredient therein.

The active ingredient may also be presented in a formulation comprising micrometer- or nanometer-size particles of active ingredient, which formulation may contain other pharmaceutical agents and may optionally be converted to solid form.

Preferred unit dosage formulations are those containing a daily dose or unit daily sub-dose (as herein above recited) or an appropriate fraction thereof, of the active ingredient.

It should be understood that in addition to the ingredients particularly mentioned above the formulation of this invention may include other agents conventional in the art having regard to the type of formulation in question, for example those suitable for oral administration may include flavoring agents or taste masking agents.

It will be further understood that the compound of formula (I) may be combined with one or more other HIV anti-viral agents, for example Reverse Transcriptase Inhibitors (RTIs), Non Nucleoside Reverse Transcriptase Inhibitor (NNRTIs), and other HIV protease inhibitors.

Examples of suitable RTIs include zidovudine, didanosine (ddI), zalcitabine (ddC), stavudine (d4T), abacavir, iamivuidine (3TC) and FTC.

Examples of suitable NNRTIs include HEPT, TIBO derivatives, atevirdine, L-ofloxacin, L-697,639, L-697,661, nevirapine (BI-RG-587), loviride (α-APA), delavuridine (BHAP), phosphonoformic acid, benzodiazepinones, dipyridodiazepinones, 2-pyridones, bis(heteroaryl) piperazines, 6-substituted pyrimidines, imidazopyridazines, 1,4-dihydro-2H-3,1-benzoxazin-2-ones, such as (−)-6-chloro4-cyclopropylethynyl-4-trifluoromethyl-1,4-dihydro-2H-3,1-benzoxazin-2-one (L-743,726 or DMP-266), and quinoxalines, such as isopropyl (2S)-7-fluoro-3,4-dihydro-2-ethyl-3-oxo-1-(2H)-quinoxalinecarboxylate (HBY 1293) or HBY 097.

Examples of suitable HIV protease inhibitors include those disclosed in WO 94/05639, WO 95/24385, WO 94/13629, WO 92/16501, WO 95/16688, WO/US94/13085, WO/US94/12562, US 93/59038, EP 541168, WO 94/14436, WO 95/09843, WO 95/32185, WO 94/15906, WO 94/15608, WO 94/04492, WO 92/08701, WO 95/32185, and U.S. Pat. No. 5,256,783, in particular (S)-N-((.alpha.S)-

((1R)-2-((3S,4αS,8αS)-3-(tert-Butylcarbamoyl)octahydro-2(1H)-isoquinolyl)-1-hydroxyethyl)phenethyl)-2-quinaldaminosuccinamide monomethanesulfonate (saquinavir), N-(2(R)-Hydroxy-1(S)indanyl)-2(R)-(phenylmethyl)4(S)-hydroxy-5-[1-[4-(3-pyridylmethyl)-2(S)-(N-tert-butylcarbamoyl)piperazinyl]]pentaneamide (indinavir), 10-hydroxy-2-methyl-5-(1-methylethyl)-1-[2-(1-methylethyl)4-thiazolyl]-3,6-dioxo-8,11-bis(phenylmethyl)-2,4,7,12-tetraazatridecan-13-oic acid, 5-thiazolylmethyl ester (ritonavir), (N-(1,1-dimethyl)decahydro-2-[2-hydroxy-3-[(3-hydroxy-2-methylbenzoyl)amino]4-(phenylthio)butyl]-3-isoquinolinecarboxamide monomethanesulfonate (nelfinavir), and related compounds.

The compound of formula (I) and combinations thereof with RTIs, NNRTIs and/or HIV protease inhibitors are especially useful for the treatment of AIDS and related clinical conditions such as AIDS related complex (ARC), progressive generalized lymphadenopathy (PGL), Kaposi's sarcoma, thrombocytopenic purpura, AIDS-related neurological conditions such as AIDS dementia complex, multiple sclerosis or tropical paraperesis, and also anti-HIV antibody-positive and HIV-positive conditions, including such conditions in asymptomatic patients.

The following examples are intended for illustration only and are not intended to limit the scope of the invention in any way.

EXAMPLE 1

Preparation of Calcium (3S) tetrahydro-3-furanyl (1S,2R)-3-[[(4-amino-phenyl)-sulfonyl](isobutyl)amino]-1-benzyl-2-phosphonooxy)propyl-carbamate (I) from (3S) tetrahydro-3-furanyl (1S,2R)-3-[[(4-aminophenyl)-sulfonyl](isobutyl)amino]-1-benzyl-2-(phosphonooxy)propylcarbamate (III)

(3S) tetrahydro-3-furanyl (1S,2R)-3-[[(4-aminophenyl)sulfonyl](isobutyl)amino]-1-benzyl-2-(phosphonooxy)propylcarbamate (10 g) was dissolved in industrial methylated spirit (60 ml) and heated to 50° C. A solution of calcium acetate (2.43 g) in water (60 ml) was added slowly, causing a white crystalline precipitate to form. The mixture was allowed to cool slowly to 20° C. The solid was filtered off, washed with industrial methylated spirit/water (1:1, 2×25 ml) and water (25 ml), then dried in vacuo at 20° C. to give the title compound as white microcrystalline needles (7.52 g).

NMR (Solvent 0.1N DCl in $D_2O$) 0.8–0.9 ppm (m 6H), 1.2–1.3 ppm (m, 0.5H), 1.85–2.2 ppm (m, 2.5H), 2.6–2.75 ppm (m, 1H, J=13.0 Hz), 2.9–3.2 ppm (m, 3H), 3.34 (m 1H) 3.42 ppm (d, 1H, J=10.8 Hz), 3.55–3.9 ppm (m, 4H), 4.2–4.3 ppm (m, 1H, J=10.3 Hz), 4.55 ppm (m 1H), 4.8–5.0 ppm (m, 1H masked by HOD signal), 7.3–7.4 ppm (m, 5H), 7.6–7.7 ppm (m, 2H, J=8.3 Hz), 8.0–8.1 ppm (d, 2H, J=8.8 Hz). Ethanol content by NMR 2.7% w/w.

Melting Point 282–284° C. (dec)

EXAMPLE 2

Preparation of Calcium (3S) tetrahydro-3-furanyl (1S,2R)-3-[[(4-aminophenyl)-sulfonyl](isobutyl)amino]-1-benzyl-2-(phosphonooxy)propyl-carbamate (I) from (3S) tetrahydro-3-furanyl (1S,2R)-3-[[(4-nitrophenyl)-sulfonyl](isobutyl)amino]-1-benzyl-2-(phosphonooxy)propylcarbamate (IV)

A solution of (3S) tetrahydro-3-furanyl (1S,2R)-3-[[(4-nitrophenyl)sulfonyl]-(isobutyl)amino]-1-benzyl-2-(phosphonooxy)propylcarbamate (17.34 g) in industrial methylated spirit (68 ml) and water (17 ml) was treated with 10% palladium on carbon catalyst (3.4 g). The mixture was stirred under hydrogen at ambient temperature for 3 h. The catalyst was filtered off, washing with industrial methylated spirit (34 ml). The filtrate was warmed to 50° C. and a solution of calcium acetate (4.45 g) in water (85 ml) was added slowly, causing a white crystalline precipitate to form. The mixture was allowed to cool slowly to 20° C. The solid was filtered off, washed with industrial methylated spirit/water (1:2, 2×25 ml), then dried in vacuo at 20° C. to give the title compound as white microcrystalline needles (14.04 g).

NMR (Solvent 0.1N DCl in $D_2O$) 0.65–0.75 ppm (m 6H), 1.1–1.2 ppm (m, 0.5H), 1.7–2.05 ppm (m, 2.5H), 2.45–2.55 ppm (m, 1H, J=13.0 Hz), 2.8–3.05 ppm (m, 3H), 3.15 (m, 1H) 3.3 ppm (d, 1H, J=10.8 Hz), 3.4–3.8 ppm (m, 4H), 4.05–4.15 ppm (m, 1H, J=10.3 Hz), 4.35 ppm (m 1H), 4.6–4.8 ppm (m, 1H masked by HOD signal), 7.3–7.4 ppm (m, 5H), 7.6 ppm (m, 2H, J=8.3 Hz), 7.9 ppm (d, 2H, J=8.3 Hz). Signals shifted upfield due to lost lock. Ethanol content by NMR 3.4% w/w.

Water content by Karl Fisher analysis is 11.1% w/w.

EXAMPLE 3

Preparation of Calcium (3S) tetrahydro-3-furanyl (1S,2R)-3-[[(4-aminophenyl)-sulfonyl](isobutyl)amino]-1-benzyl-2-(phosphonooxy)propyl-carbamate (I) from (3S) tetrahydro-3-furanyl (1S,2R)-3-[[(4-nitrophenyl)-sulfonyl](isobutyl)amino]-1-benzyl-2-(hydroxy)propylcarbamate (II)

Phosphorus oxychloride (69 ml) was added to a suspension of (3S) tetrahydro-3-furanyl (1S,2R)-3-[[(4-nitrophenyl)sulfonyl](isobutyl)amino]-1-benzyl-2-(hydroxy)propylcarbamate (300 g) in pyridine (450 ml) and methyl-isobutylketone (1500 ml). After stirring at 25–30° C. for 2.5 h, phosphorus oxychloride (7 ml) was added. After a further 1 h, the resulting suspension was added to 6M hydrochloric acid (500 ml). The mixture was then heated at 50–55° C. for 2 h, then cooled. The phases were separated and the aqueous phase was extracted with methyl-isobutylketone (600 ml). The combined organic solutions were washed with water (2×600 ml).

The methyl-isobutylketone solution was concentrated to ca 600 ml in vacuo and then water (1500 ml) and sodium bicarbonate (94. g) were added. After stirring for 20 minutes, the phases were separated, and the aqueous solution was washed with ethyl acetate (3×200 ml). The aqueous solution was treated with 10% palladium on carbon catalyst (30 g), left under vacuum for 5 minutes, treated with industrial methylated spirit (1200 ml) then stirred under hydrogen at below 30° C. for 2.5 h. The catalyst was filtered off, washing with industrial methylated spirit (600 ml).

The filtrate was warmed to 40–50° C. and a solution of calcium acetate monohydrate (99.5 g) in water (300 ml) was added over 20 minutes, then the resulting suspension was stirred at 40–50° C. for 30 minutes, then cooled to ambient temperature over 30 minutes. The product was filtered and washed with industrial methylated spirit/water (1:1, 2×600 ml), then dried in vacuo at 35–40° C. to give the title compound as white microcrystalline needles (293.28 g).

NMR (Solvent 0.1N DCl in $D_2O$) 0.8–0.9 ppm (m 6H), 1.2–1.3 ppm (m, 0.5H), 1.85–2.2 ppm (m, 2.5H), 2.6–2.75 ppm (m, 1H, J=13.0 Hz), 2.9–3.2 ppm (m, 3H), 3.34 (m 1H) 3.42 ppm (d, 1H, J=10.8 Hz), 3.55–3.9 ppm (m, 4H), 4.2–4.3 ppm (m, 1H, J=10.3 Hz), 4.55 ppm (m 1H), 4.8–5.0 ppm (m, 1H masked by HOD signal), 7.3–7.4 ppm (m, 5H), 7.6–7.7 ppm (m, 2H, J=8.3 Hz), 8.0–8.1 ppm (d, 2H, J=8.8 Hz). Ethanol content by NMR 1.7% w/w.

EXAMPLE 4

Recrystallisation of Calcium (3S) tetrahydro-3-furanyl (1S,2R)-3-[[(4-amino-phenyl)sulfonyl (isobutyl)amino]-1-benzyl-2-(phosphonooxy)propyl-carbamate (I)

Calcium (3S) tetrahydro-3-furanyl (1S,2R)-3-[[(4-aminophenyl)sulfonyl]-(isobutyl)amino]-1-benzyl-2-(phosphonooxy)propylcarbamate (5 g; prepared in a similar manner to that described in any of examples 1,2 or 3) was suspended in industrial methylated spirit (75 ml) and heated to 70° C. The mixture was clarified through a bed of filter-aid, washing through with industrial methylated spirit (25 ml). The filtrate was reheated to 70° C., then water (15 ml) was added. The resulting suspension was slowly cooled to 20° C., then the product was filtered off, washed with industrial methylated spirit/water (1:1, 2×10 ml), then dried in vacuo at 20° C. to give the title compound as white microcrystalline needles (4.58 g).

NMR (Solvent 0.1N DCl in $D_2O$) 0.8–0.9 ppm (m 6H), 1.2–1.3 ppm (m, 0.5H), 1.85–2.2 ppm (m, 2.5H), 2.6–2.75 ppm (m, 1H, J=13.0 Hz), 2.9–3.2 ppm (m, 3H), 3.34 (m 1H) 3.42 ppm (d, 1H, J=10.8 Hz), 3.55–3.9 ppm (m, 4H), 4.2–4.3 ppm (m, 1H, J=10.3 Hz), 4.51 ppm (m 1H), 4.8–5.0 ppm (m, 1H masked by HOD signal), 7.3–7.4 ppm (m, 5H), 7.6–7.7 ppm (m, 2H, J=8.3 Hz), 8.0–8.1 ppm (d, 2H, J=8.8 Hz). Ethanol content by NMR 3.1% w/w.

Melting Point 282–284° C. (dec)

EXAMPLE 5

Preparation of Calcium (3S) tetrahydro-3-furanyl (1S,2R)-3-[[(4-aminophenyl)-sulfonyl](isobutyl) amino]-1-benzyl-2-(phosphonooxy)propyl-carbamate (I) from (3S) tetrahydro-3-furanyl (1S, 2R)-3-[[(4-nitrophenyl)-sulfonyl](isobutyl)amino]-1-benzyl-2-(hydroxy)propylcarbamate (II)

Phosphorus oxychloride (24.1 kg) was added to a suspension of (3S) tetrahydro-3-furanyl (1S,2R)-3-[[(4-nitrophenyl)sulfonyl](isobutyl)amino]-1-benzyl-2-(hydroxy)propylcarbamate (37 kg) in pyridine (48.5 kg) and methyl-isobutylketone (170 L). After stirring at 25–30° C. for 2.5 h, the resulting suspension was added to 2N hydrochloric acid (120 L). The mixture was then heated at 65–70° C. for 3 h, then cooled. The phases were separated and the aqueous phase was extracted with methyl-isobutylketone (70 L). The combined organic solutions were washed with water (2×70 L).

The methyl-isobutylketone solution was concentrated to ca 70 L in vacuo and then water (150 L) and 32% sodium hydroxide (14.3 kg) were added. After stirring for 15 minutes, the phases were separated, and the aqueous solution was washed with methyl-isobutylketone (3×34 L). The aqueous solution was treated with 5% palladium on carbon catalyst (1.7 kg), treated with industrial methylated spirit (136 L) then stirred under hydrogen at below 30° C. for 8 h. The catalyst was filtered off, washing with industrial methylated spirit (170 L).

The filtrate was warmed to 40–50° C. and a solution of calcium acetate hydrate (9.5 kg) in water (136 L) was added over 2 h, then the resulting suspension was stirred at 40–50° C. for 30 minutes, then cooled to ambient temperature over 2 h. The product was filtered and washed with industrial methylated spirit/water (1:1, 2×68 L), then water (2×68 L). The product was then stirred and heated with water (340 L) for 4 h at 90–95° C. then cooled to 20–25° C. The solid was filtered and washed with industrial methylated spirits (3×34 L) then dried in vacuo at 35–40° C. to give the title compound as white microcrystalline needles (25.8 kg).

NMR (Solvent 0.1N DCl in $D_2O$) 0.8–0.9 ppm (m 6H), 1.2–1.3 ppm (m, 0.5H), 1.85–2.2 ppm (m, 2.5H), 2.6–2.7 ppm (m, 1H, J=13.0 Hz), 2.9–3.2 ppm (m, 3H), 3.3–3.4 ppm (m 1H) 3.42 ppm (d, 1H, J=10.8 Hz), 3.55–3.9 ppm (m, 4H), 4.2–4.3 ppm (m, 1H, J=10.3 Hz), 4.5 ppm (m 1H), 4.8–5.0 ppm (m, 1H masked by HOD signal), 7.3–7.4 ppm (m, 5H), 7.6–7.7 ppm (m, 2H, J=8.3 Hz), 8.0–8.1 ppm (d, 2H, J=8.8 Hz). Ethanol content by NMR 1.0% w/w.

Water content by Karl Fisher analysis is 10.9% w/w.

EXAMPLE 6

Tablet Formulation

| Ingredient | Actual mg/tablet |
| --- | --- |
| Compound of formula (I) | 576.1* |
| Microcrystalline Cellulose, NF | 102.2 |
| Croscarmellose Sodium | 38.0 |
| Povidone, USP | 34.2 |
| Colloidal Silicon Dioxide, NF | 1.9 |
| Magnesium Stearate, NF | 7.6 |
| Total | 760 |

*weight of calcium salt, equivalent to 465 mg free acid based on a 1.239 factor

Preparation Method

First, the components are weighed from bulk containers and then sieved using a Russell-SIV equipped with 14 mesh (1.4 mm opening) or an equivalent sieve and mesh, and deposited into a stainless-steel blending container.

The compound of formula (I), microcrystalline cellulose NF, croscarmellose sodium, povidone USP and colloidal silicon dioxide NF are blended for 20 minutes using a suitable blender, such as a Matcon-Buls bin-type blender, a V-blender or equivalent. The magnesium stearate is then added to the mixture and blending is continued for approximately 2 minutes.

The blend is then compressed using a suitable rotary tablet press, typically a Courtoy R-190, R-200 or equivalent. In-process controls for tablet weight and hardness are applied at appropriate intervals throughout the compression run and adjustments to the tablet press are made as necessary.

Relative Oral Bioavailability of the Compound of Formula (I) Compared to Amprenavir in Beagle Dogs The relative oral bioavailability of the compound of formula (I) was measured in Beagle dogs, as compared to the bioavailability of amprenavir (141W94) in the same animals. This existing model had previously been used for testing the oral bioavailability of amprenavir and other compounds. The results were obtained from dosing in three animals.

Oral dosing of the compound of formula (I) directly to the dogs resulted in a relative bioavailability of 23.8±23.8% as compared to amprenavir.

Oral dosing of the compound of formula (I) to dogs given an oral gavage of 0.1N HCl before administration of the drug, resulted in a relative bioavailability of 58.4±11.5% as compared to amprenavir.

These results suggested that the compound of formula (I) was less bioavailable than amprenavir itself. However, the pH in the stomach of dogs is typically much higher than in man.

Aqueous Solubility

The aqueous solubility of amprenavir is 0.095 mg/ml at pH 6.3, and the solubility in 0.1N Hcl (~pH 1) is 0.29 mg/ml.

The aqueous solubility profile of the compound of formula (I) is pH 6.27 0.531 mg/ml pH 5.02 3.20 mg/ml pH 4.11 9.41 mg/ml pH 3.27 61.1 mg/ml pH 1.47 3.20 mg/ml These data illustrate the surprisingly increased and pH dependent aqueous solubility of the compound of formula (I) as compared to amprenavir. The solubility is notably good between about pH 3 and 4.

TABLE 1

Angles 2θ and their relative intensities compared to the strongest peak for the X-ray powder diffraction pattern of the compound of formula (I)

| Angle 2θ | rel. int. |
|---|---|
| 5.7350 | 100 |
| 9.9450 | 38 |
| 11.1150 | 7 |
| 11.5000 | 10 |
| 13.7800 | 18 |
| 14.9300 | 10 |
| 15.2250 | 16 |
| 17.9800 | 35 |
| 19.7450 | 14 |
| 19.9600 | 5 |
| 20.8050 | 8 |
| 21.5750 | 12 |
| 22.1700 | 15 |
| 22.3550 | 7 |
| 22.9100 | 6 |
| 23.1350 | 5 |
| 24.5050 | 14 |
| 25.0350 | 2 |
| 25.2550 | 2 |
| 25.8600 | 7 |
| 26.5050 | 2 |
| 27.0200 | 10 |
| 27.7850 | 3 |
| 28.2150 | 4 |
| 28.3650 | 6 |
| 28.8250 | 2 |
| 28.9450 | 2 |
| 29.4150 | 4 |
| 30.1950 | 2 |
| 30.5750 | 3 |
| 31.1200 | 2 |
| 31.7950 | 2 |
| 32.2450 | 4 |
| 32.7750 | 3 |
| 32.8900 | 3 |
| 33.8150 | 2 |
| 34.9050 | 2 |
| 35.2950 | 3 |
| 35.8050 | 2 |
| 36.4600 | 3 |
| 36.8300 | 2 |

TABLE 1-continued

Angles 2θ and their relative intensities compared to the strongest peak for the X-ray powder diffraction pattern of the compound of formula (I)

| Angle 2θ | rel. int. |
|---|---|
| 37.8400 | 2 |
| 38.6550 | 2 |
| 39.5350 | 2 |
| 39.6150 | 2 |
| 40.5850 | 3 |
| 41.3550 | 2 |
| 41.8100 | 2 |
| 42.2350 | 2 |
| 42.6900 | 3 |
| 43.2000 | 2 |
| 43.9200 | 1 |
| 44.4000 | 2 |

What is claimed is:

1. Calcium (3S) tetrahydro-3-furanyl(1S,2R)-3-[[(4-aminophenyl)sulfonyl](isobutyl)amino]-1-benzyl-2-(phosphonooxy)propylcarbamate Form (1).

2. A pharmaceutical composition comprising a compound as claimed in claim 1 together with at least one pharmaceutically acceptable diluent or carrier therefor.

3. A method for the treatment of an HIV infection in a human which comprises administering to said human, an effective anti-HIV infection treatment amount of a compound as claimed in claim 1.

4. A pharmaceutical composition according to claim 2 in the form of a powder.

5. A pharmaceutical composition according to claim 2 in the form of a suspension.

6. A pharmaceutical composition according to claim 2 in the form of a tablet.

7. A process for the preparation of a compound of formula (I) in a crystalline form,

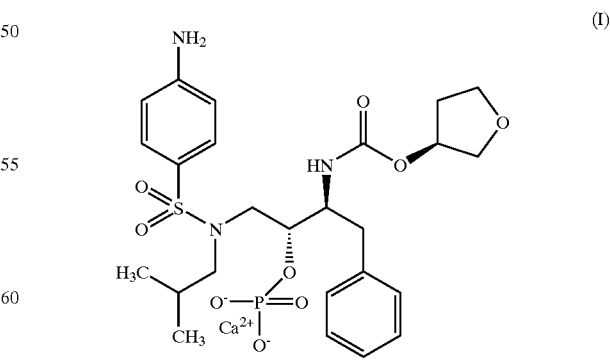

comprising i) reacting a compound of formula (II)

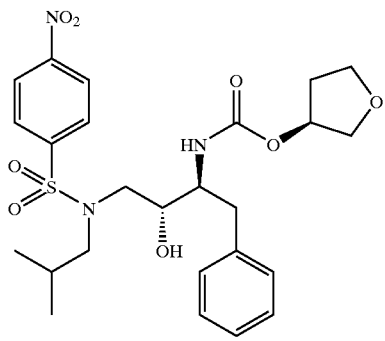

with a phosphorylating agent;

ii) reducing the resultant compound with a reducing agent in a suitable solvent; and iii) adding to the resultant compound a source of calcium ions in the presence of a suitable solvent.

8. A process for the preparation of a compound of formula (I)

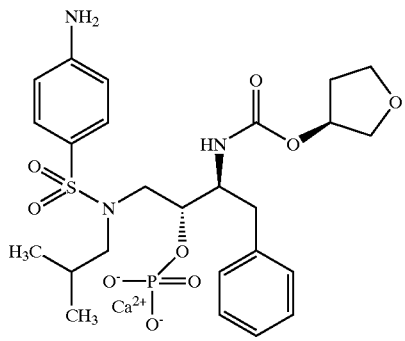

comprising dissolving a compound of formula (III)

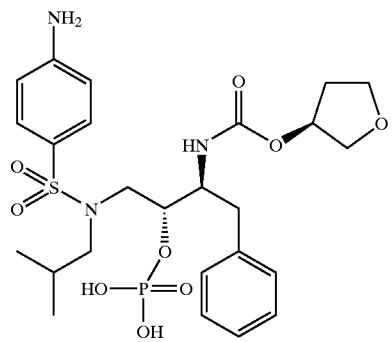

in a suitable solvent, and adding to the solution water and a source of calcium ions.

9. A process for the preparation of a compound of formula (I)

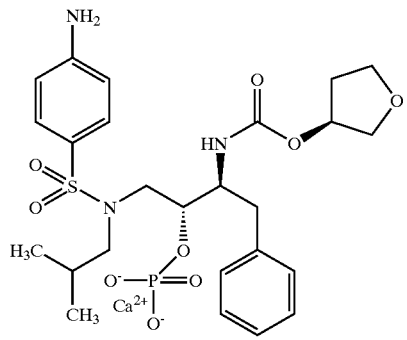

comprising the reduction of a compound of formula (IV)

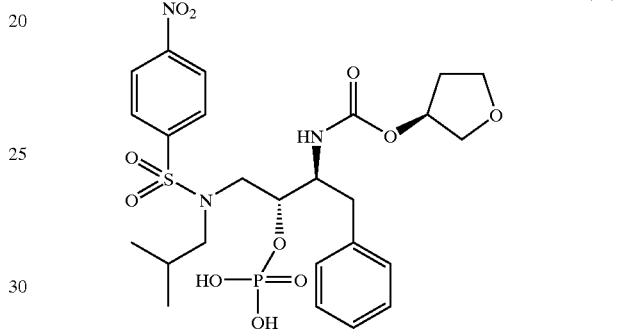

in the presence of a suitable reducing agent in a suitable solvent, followed by adding water and a source of calcium ions.

10. A process for the preparation of a compound of formula (I) as claimed in claim 7, wherein the phosphorylating agent is phosphorus oxychloride.

11. A process for the preparation of a compound of formula (I) as claimed in claim 7, wherein the phosphorylating agent is added in the presence of a base.

12. A process for the preparation of a compound of formula (I) as claimed in claim 7, wherein the product of step i) is converted to its sodium salt prior to step ii).

13. A process for the preparation of a compound of formula (I) as claimed in claim 7, wherein the reducing agent is hydrogen with a palladium on carbon catalyst.

14. A process for the preparation of a compound of formula (I) as claimed in claim 7, wherein the calcium ion source is calcium acetate.

15. A process for the preparation of a compound of formula (I) as claimed in claim 7, additionally comprising recrystallising the compound from an appropriate solvent.

16. A process for the preparation of a compound of formula (I) as claimed in claim 15, wherein the solvent is a mixture of industrial methylated spirit and water.

17. A process for the preparation of a compound of formula (I) as claimed in claim 7, additionally comprising heating the product in water to a temperature in the range 70 to 99° C. for 2.5 to 6 hours, then cooling to ambient temperature and harvesting to solid.

18. Calcium (3S) tetrahydro-3-furanyl(1S,2R)-3-[[(4-aminophenyl)sulfonyl](isobutyl)amino]-1-benzyl-2-(phosphonooxy)propylcarbamate Form (1) characterized by an X-ray powder diffraction trace substantially as shown in FIG. 1.

19. A crystalline form of calcium (3S) tetrahydro-3-furanyl(1S,2R)-3-[[(4-aminophenyl)sulfonyl](isobutyl)

amino]-1-benzyl-2-phosphonooxy)propylcarbamate characterised by an X-ray powder diffraction pattern expressed in terms of 2 theta angles, wherein said X-ray powder diffraction pattern has peaks that may occur at the following approximate 2 theta angles: 5.735, 9.945, 11.500, 13.780, 14.930, 15.225, 17.980, 19.745, 21.575, 22.170, 24.505 and 27.020 degrees.

20. A crystalline form of calcium (3S) tetrahydro-3-furanyl(1S,2R)-3-[[(4-aminophenyl)sulfonyl](isobutyl)amino]-1-benzyl-2-(phosphonooxy)propylcarbamate characterised by an X-ray powder diffraction pattern expressed in terms of 2 theta angles and relative intensities (1),

| Angle 2θ | I |
|---|---|
| 5.7350 | 100 |
| 9.9450 | 38 |
| 11.1150 | 7 |
| 11.5000 | 10 |
| 13.7800 | 18 |
| 14.9300 | 10 |
| 15.2250 | 16 |
| 17.9800 | 35 |
| 19.7450 | 14 |
| 19.9600 | 5 |
| 20.8050 | 8 |
| 21.5750 | 12 |
| 22.1700 | 15 |
| 22.3550 | 7 |
| 22.9100 | 6 |
| 23.1350 | 5 |
| 24.5050 | 14 |
| 25.0350 | 2 |
| 25.2550 | 2 |
| 25.8600 | 7 |
| 26.5050 | 2 |
| 27.0200 | 10 |
| 27.7850 | 3 |
| 28.2150 | 4 |
| 28.3650 | 6 |
| 28.8250 | 2 |
| 28.9450 | 2 |
| 29.4150 | 4 |
| 30.1950 | 2 |
| 30.5750 | 3 |
| 31.1200 | 2 |
| 31.7950 | 2 |
| 32.2450 | 4 |
| 32.7750 | 3 |
| 32.8900 | 3 |
| 33.8150 | 2 |
| 34.9050 | 2 |
| 35.2950 | 3 |
| 35.8050 | 2 |
| 36.4600 | 3 |
| 36.8300 | 2 |
| 37.8400 | 2 |
| 38.6550 | 2 |
| 39.5350 | 2 |
| 39.6150 | 2 |
| 40.5850 | 3 |
| 41.3550 | 2 |
| 41.8100 | 2 |
| 42.2350 | 2 |
| 42.6900 | 3 |
| 43.2000 | 2 |
| 43.9200 | 1 |
| 44.4000 | 2. |

* * * * *